United States Patent [19]

Borowski et al.

[11] 4,086,141

[45] Apr. 25, 1978

[54] PROCESS FOR THE FERMENTATION PRODUCTION OF ERGOLINE DERIVATIVES

[75] Inventors: Eva Borowski; Klaus Braun, both of Radebeul; Klaus Breuel, Dresden; Christoph Dauth, Radebeul; Dieter Erge, Halle; Werner Grawert, Radebeul; Detlev Gröger, Halle; Liselotte Höhne, Dresden; Edda Knothe; Monika Müller, both of Radebeul; Gisela Nordmann, Dresden; Rudolf Schirutschke, Radebeul; Klaus-Dieter Volzke, Dresden, all of Germany

[73] Assignee: VEB Arzneimittelwerk Dresden, Radebeul, Germany

[21] Appl. No.: 740,137

[22] Filed: Nov. 8, 1976

[51] Int. Cl.² ............................................. C12D 13/02
[52] U.S. Cl. .................................................. 195/81
[58] Field of Search .................................... 195/32, 81

[56] References Cited

U.S. PATENT DOCUMENTS

| | | | |
|---|---|---|---|
| 2,809,920 | 10/1957 | Stoll et al. | 195/81 |
| 3,110,651 | 11/1963 | Kybal et al. | 195/81 |
| 3,276,972 | 10/1966 | Amici et al. | 195/81 |
| 3,658,653 | 4/1972 | Amici et al. | 195/81 |

*Primary Examiner*—Alvin E. Tanenholtz
*Attorney, Agent, or Firm*—Michael J. Striker

[57] ABSTRACT

Ergoline derivatives including alkaloids and 9,10-dihydroalkaloids of the ergotoxine group and including ergometrine are made by forming a submerged culture under aerobic conditions by inoculation of an aqueous medium containing a carbon source, an organic or inorganic nitrogen source or both of these sources, and nutrient salts, the inoculum being spores obtained from a strain of *Claviceps purpurea* (Fr.) Tul. deposited under number IMET PA 130, and then, after completion of the cultivation, extracting the formed alkaloids from the culture and, if necessary, 9,10-dihydrogenating the extracted alkaloids, and converting the alkaloids into pharmaceutically acceptable acid addition salts.

22 Claims, No Drawings

PROCESS FOR THE FERMENTATION PRODUCTION OF ERGOLINE DERIVATIVES

BACKGROUND OF THE INVENTION

The invention relates to a process for the industrial production of ergoline derivatives including alkaloids and 9,10-dihydroalkaloids of the ergotoxine group and including also ergometrine.

These alkaloids and 9,10-dihydroalkaloids are known for their high therapeutic usefulness and are employed in internal medicine, neurology and gynecology.

The industrial recovery of ergot alkaloids up to now has been carried out on a large scale by agricultural growing of alkaloid type sclerotia of the microorganism *Claviceps purpurea* which exists as a parasite on rye. To avoid the difficulties involved in this type of production attempts have been made to cause the organism to form alkaloids also under non-parasitic conditions. It has been found however that only very few strains of Claviceps were useful for this purpose and only when grown particularly therefor. Only with these few strains and only in specially set-up media could the biosynthesis of ergot alkaloids be effected.

Since the composition of the alkaloid spectrum of these strains depends considerably on the different genetic conditions only a portion of the strains forms alkaloids of the ergotoxine groups which are sufficiently differentiated therapeutically in the general group of ergot alkaloids of the peptide type.

The existence of a few such strains has been described in detail in Hungarian Pat. No. 150,631, patent of the German Democratic Republic No. 41,967, British Pat. No. 1,158,380, and patents of the Federal Republic of Germany, Nos. 1,806,984 and 1,909,216. Nevertheless, the problem of a saprophytic production of alkaloids of the ergotoxine group alone or in combination with other ergot alkaloids has not been solved insofar as production on an industrial scale is concerned.

For a continuous production the requirement is that a high performance starting material of the strain must be currently available in large amounts as inoculum for the fermentation process and that production must be possible in a simple and definite manner.

The customary and best method in technical microbiology is the use of special reproduction units of the organism (conidiospores) which provide for a stable source of the desired properties of the strain throughout many years by means of lyophilized spores containing cans, that is, without the complicated and laborious strain preservation as described in German Pat. No. 1,206,384, but also because the large numbers of conidiospores per volume unit-permits to inoculate large amounts of nutrient medium with a small amount of inoculum.

All this requires a specific characteristic of the strain which is determined by its heritable disposition to form under proper conditions a large number of spores having a high potency for the biosynthesis of the alkaloids. The inoculation of the culture medium can then be carried out very well on an industrial scale favorably using a suspension of conidiospores.

It is this property however which is lacking in the prior art strains of Claviceps which form alkaloids of the ergotoxine group in saprophytic cultures. This shortcoming appears clearly from Hungarian Pat. No. 150,631 and from AMICI et al. (Appl. Microbiology 18 (1969), pp. 464–468). The conditions for the formation of seed cultures on an industrial scale are not good in these cases because of the necessity for reproduction of the inoculum on solid substrata and for homogenization of the thus obtained mycelium.

The publications cited also show that up to the end of the fermentation process with these ergotoxine forming microorganism only a small portion of the ergotoxine which is formed in the cells will permeate the cell walls and enter the surrounding aqueous culture medium.

In order to carry out a complete production of the formed alkaloids the separate processing both of the culture filtrate and the mycelium is necessary. The high pigment and dead weight portion formed usually in strains which are adapted for biosynthesis of ergot alkaloids in submersed cultures requires highly complicated operations and results in unsatisfactory yields.

Thus, according to the British Pat. No. 1,158,380, the obtained culture filtrate is extracted with chloroform at pH 9, the obtained extract is then extracted with aqueous tartaric acid and the resulting aqueous extract is again extracted with chloroform at pH 9 and the latter extract is finally united with the mycelium extract which has been obtained and purified in a similar complicated manner, and is then concentrated by evaporation whereupon the crude alkaloid bases are finally precipitated with hexane. From the precipitate ergotamine sulfate is removed with glacial acetic acid, methanol and sulfuric acid, the residue is concentrated by evaporation, an aqueous solution thereof is extracted at pH 9 again with chloroform, the concentrated chloroform extract is subjected to chromatography through 100 times the amount of silica gel and the thus purified ergocryptine is finally isolated as base from benzene. By means of a further chromatographic fraction additional ergotamine can be obtained after concentration by evaporation and solution of the residue in aqueous acetone.

The directions of British Pat. No. 1,158,380 and U.S. Pat. No. 3,485,722 for isolating ergot peptide alkaloids from cultures of a new strain of *Claviceps purpurea* likewise had no success. Disturbing in this case was particularly the strong tendency of the culture filtrate and of the mycelium extract to form emulsions during chloroform extraction. Furthermore, it was not possible to convert the ergotoxin into a crystalline base and to obtain the yields of noncrystalline pure or crude alkaloid concentrates mentioned in the above patent.

The Pat. No. 41,967 of the German Democratic Republic describes a process wherein an extract which is obtained in known manner from a culture medium which contains a low alkaloid concentration is subjected to chromatography with increasingly polar eluants whereupon the individual alkaloids are crystallized in conventional manner. The extract in this case contained ergotoxin and ergometrine together. However, it is well known that the elution with methanol-containing solvents results in unsatisfactorily high pigment fractions in the ergometrine.

According to the German Pat. No. 883,153 and the Canadian Pat. No. 470,573 the pressure hydrogenation of ergotoxin is carried out with highly active palladium or carrier supported palladium. This type of process apparently due to an unsatisfactory selectivity resulted in undesirable pigmentation of the hydrogenation product which again required additional purification operations.

It is therefore an object of the invention to provide for a process for the industrial production of ergoline derivatives, in particular alkaloids and 9,10-dihydroalkaloids of the ergotoxin group and also of ergometrine which avoids these shortcomings.

SUMMARY OF THE INVENTION

In the process of the invention the ergoline derivatives are formed by means of a submerged culture, under aerobic conditions, which is produced by inoculating an aqueous medium containing a carbon source, an organic or inorganic nitrogen source or both of these sources and nutrient salts, the inoculum being spores obtained from a strain of *Claviceps purpurea* (Fr.) Tul. deposited under number IMET PA 130, and then, after completion of the cultivation, extracting the formed alkaloids from the culture, 9,10-dihydrogenating, if necessary, the extracted alkaloids and converting the alkaloids into pharmaceutically acceptable acid addition salts.

The invention in particular is based on the finding that the strain of *Claviceps purpurea* (Fr.) Tul. which is grown by means of artificial nutrient media containing inorganic or organic nitrogen sources, sugar, organic acids and conventional inorganic salts can produce, in a submerged culture, alkaloids of the ergotoxin group, ergometrine and other ergoline derivatives and that this alkaloid synthesis is possible on a scale useful for industrial exploitation. In particular it has been found that this strain in solid or liquid media under specific conditions will form a large amount of spores having a high potency for the alkaloid synthesis and for long time storage.

In addition the formed ergotoxine is found in large amounts and the ergometrine is found virtually quantitatively in the fermentation medium surrounding the mycelium.

It has furthermore been found that by filtering the culture medium of the new strain the filtrate can be extracted with lower alkyl carboxylic acid esters, preferably ethyl acetate. Preferably the filtrate is diluted with an equal volume of water. The filtrate furthermore is adjusted by means of ammonia to a pH 8 to 9. If the filtrate is diluted with water the extraction can also be carried out with chlorinated hydrocarbons, preferably methylene chloride in a virtually complete manner and without any interfering formation of an emulsion. With the dilute culture medium a substantial increase of the ergotoxine amount in the filtrate is surprisingly obtainable in addition to the lowering of the contents of dead weight material.

The biomass which results from the filtration, depending on the residual alkaloid contents, may be extracted with acetone and the clear extract resulting from the filtration may be purified after adjustment with an aqueous acid, preferably, phosphoric acid to a pH of 2-3 by means of hydrocarbon mixtures such as petroleum ether or petroleum ether-xylene. The separated aqueous phase can then be extracted after adjustment of the pH to 8-9 with aqueous ammonia solution by means of lower alkyl carboxylic acid esters, preferably ethylacetate and the resulting extract is then washed with water.

It has furthermore been found that it is possible, in a surprisingly elegant manner, to extract the ergot alkaloid also directly from the culture liquid of the *Claviceps purpurea* strain which has been alkalized with ammonia without preceding separation of the biomass. The extraction is carried out after addition of ammonium sulfate with lower alkyl carboxylic acid esters, preferably ethyl acetate. The extract can then be purified of undesired contamination by a liquid-liquid extraction with dilute aqueous acids, preferably phosphoric acid and subsequent liquid-liquid extraction of the aqueous extract at pH 8-9 with a lower alkyl carboxylic acid ester, preferably ethylacetate.

The thus-obtained purified alkaloid extract is then concentrated by evaporation at a temperature below 30° C and the obtained concentrate can then be subjected to a further differentiating final purification of the individual alkaloids.

It has also been found that analogous to the Pat. No. 41,967 of the German Democratic Republic the pure alkaloids can be obtained by dissolving the crude alkaloid concentrate obtained as above by 1 to 3 volumes of chloroform and to keep the solutions at temperatures below +10°. Surprisingly a low-pigment ergometrine-chloroform-adduct will crystallize out in quantitative amounts. It can then be separated and converted to acid addition salts of a high degree of purity, preferably hydrogen maleinate.

The filtrate remaining after separating the ergometrine can then be concentrated without difficulties at temperatures below +30° C. Preferably it is subjected to adsorption and subsequent desorption in a batch process or to a column chromatographic operation. For this purpose aluminum oxide may preferably be used in a ratio of 1:20 or 1:5 relative to the total amount of alkaloids in the alkaloid concentrate by addition of active carbon (adsorption mean ratio: aluminum oxide: active carbon, 5:1). The extraction may be effected with lower alkyl carboxylic acid esters, preferably ethylacetate or chlorinated hydrocarbons, preferably chloroform or with a two-component mixture of these solvents or with aromatic hydrocarbons, preferably benzene after the extract or eluate have been concentrated at temperatures below 30° C. There is thus obtained an ergotoxine-ergotoxinine mixture which can be converted by crystallization from aromatic hydrocarbons, such as benzene, toluene or xylene in highly pure crystalline ergotoxine-aromatic adducts which are free of epimers. The adducts may then be converted into acid addition salts of the ergotoxine, preferably ethane sulfonate.

It has also been found that the ergotoxine which is obtained in the manner described can be hydrogenated to 9,10-dihydroergotoxine which is free of pigments. This hydrogenation can be effected in the presence of less active Raney nickel at 50° to 70° C, preferably at 60° C and at a hydrogen pressure of 30 to 70 atm above normal, preferably at 50 atm, in dioxane. The hydrogenation may also be effected in a circulation process at normal pressure and 20° to 30° C, preferably 25° C in the presence of a 5 to 10% palladium-carbon catalyst in aqueous dioxane. The hydrogenated base can then be converted in known manner into pharmaceutically acceptable acid addition salts, preferably hydrogen maleinate and ethane sulfanate.

DISCUSSION OF THE INVENTION AND OF PREFERRED EMBODIMENTS

The strain employed herein for making the inoculum and employing the inoculum in a culture for producing ergot alkaloids has been deposited with the Central Institute for Microbiology and Experimental Therapy in Jena, German Democratic Republic, which institute forms part of the German Academy of Science in Berlin. The strain has been deposited on June 29, 1972 under No. IMET PA 130.

The strain was selected from a culture which originated in a sclerotium on a test plot and which had been subjected to a mutagenic treatment.

The strain is characterized by the morphological properties summarized in the following Table.

TABLE

**Morphological Properties of *Claviceps Purpurea* Grown on Various Agar Media after 14 days Incubation in Petri Dishes at 24° C.**

Medium 1

| | | | |
|---|---|---|---|
| 3 % | saccharose | 0.001% | $FeSO . 7H_2O$ |
| 0.3 % | $NaNO_3$ | 1 % | corn steep liquor |
| 0.1 % | $K_2HPO_4$ | 3 % | agar |
| 0.05% | $MgSO_4 . 7H_2O$ | pH | 6.8–6.9 |

Structure of colony: raised, compact, irregularly and strongly folded colony; bottom side smooth, not detached from the bottom of the dish.
Diameter of the colony: 1.0 to 1.5 cm
Color of the colony: top side: light brown to violet, edge white; bottom side: brown, edge light brown.
Average number of spores: $46.3 \times 10^6$ *conidia* per colony.

Medium 2

| | | | |
|---|---|---|---|
| 15 % | beer wort | 0.1% | ammoniumcitrate |
| 0.5% | yeast extract | 3 % | agar |
| 0.5% | $(NH_4)_2PO_4$ | pH | 6.0 |

Structure of colony: center raised, with crater-like depression, intermingled with agar; edge folded radially; colony detached from bottom of the dish.
Diameter of the colony: 2 to 3 cm.
Color of the colony: top and bottom sides light grey.
Average number of spores: $34.1 \times 10^6$ *conidia* per colony.

Medium 3
2 % glucose
50% aqueous potato extract
3 % agar
pH 6.0
Structure of colony: center raised, with crater-like depressions, intermingled with agar; colony detached from the bottom of the dish.
Diameter of the colony: 1.5 to 2.0 cm.
Color of the colony: top side grey-violet; bottom side grey-brown.
Average number of spores: $3.3 \times 10^6$ *conidia* per colony.

Microscopic characteristics of the *conidia* and *hyphae*:
The *conidia* have in all cases an eliptic shape with dimensions of 6 to 10 μ (major axis) and 4 to 8 μ (minor axis). The substrate *hyphae* have a length up to 200 μ and a diameter of 4 to 8 μ. In case of bubble type swellings the diameter is 8 to 16 μ. There are aerial hyphae of a length in excess of 200 μ and of a diameter of only 2 to 4 μ.

The invention will further be illustrated in the following examples:

I. MAKING OF THE INOCULUM

For inoculation of submerged cultures conidiospores are cultivated at solid or liquid media. Further details will appear from the following three examples.

EXAMPLE 1

A base material preserved in a closed can and containing spores lyophilized in skimmed milk was suspended in beer wort (5%) and used as inoculum for growing conidiospores. The suspension was transferred to a solid medium (pH 6.0) containing 15% of beer wort, 0.5% of yeast extract, 0.5% $(NH_4)_2PO_4$, 0.1% ammonium citrate and 3% agar and was subjected to incubation in the form of a slant for 14 days at 19° C.

There were obtained in this manner $1 \times 10^{10}$ spores per culture vessel which were kept in 1000 ml Jener glass wide neck bottles as inoculum for submerged cultures. When required this inoculum should be sufficient to inoculate up to 120 liters of nutrient solution. The slants can be stored at 4° C for a year without any reduction of viability of the spores.

Example 2

An inoculum was formed by suspension of spores grown as in Example 1 which were transferred in a concentration of $1 \times 10^5$ spores/ml into a liquid medium containing 15% beer wort and 2% yeast extract. The incubation was effected at 22° C in a 500 ml round bottom flask with 120 ml liquid medium on a rotary shaking machine. After 14 days the culture contained $6 \times 10^9$ spores per flask suitable for use as inoculum for alkaloid fermentation.

Example 3

An inoculum for growing the spores was made as described in Example 1. The nutrient medium in this case was a solid medium (pH 6.8 to 6.9) which contained 3% saccharose, 0.3% $NaNO_3$, 0.1% $K_2HPO_4$, 0.05% $MgSO_4 . 7H_2O$, 0.05% KCl, 0.001% $FeSO_4 . 7H_2O$, 1% corn steep liquor and 3% agar. The incubation was effected in slants in 500 ml industrial glass narrow neck bottles and produced after 14 days incubation at 24° C, $3 \times 10^9$ spores per culture vessel which were suited as substrate for submerged cultures for the alkaloid synthesis during 10 months as far as stored at 4° C.

II. Cultures FOR THE Alkaloid Production

Preferably the incubation of the cultures is effected, generally, at a pH from 6.5 to 4.0, a time from 3 to 18 days, a temperature from 15° to 28° C and aerobic conditions. Further details will appear from the following examples.

The first three examples illustrate obtaining an extract directly from the culture medium.

Example 4

A part of the spores of an inoculum grown as described in Example 1 and stored for 9 months at 4° C was suspended and equal amounts thereof were placed into round bottom flasks of 500 ml contents. Each flask received 120 ml of a culture medium containing 10% saccharose, 1.5% ammoniumcitrate, 0.1% $Ca(NO_3)_2$, 0.025% $KH_2PO_4$, 0.01% KCl, 0.03% $MgSO_4$, 0.001% $FeSO_4$, 0.0004% $ZnSO_4$; distilled water; pH 5.5; sterilization 30 min at 0.5 at. above atmospheric.

The flasks were subjected to shaking at 24° C on a rotary shaking machine at 175 rpm under aerobic conditions. After 7 days the contents of the flasks were distributed in a ratio of 1:10 into Erlenmeyer flasks of 500 ml contents of which each received 120 ml of a culture medium containing 20% saccharose, 1% ammoniumcitrate, 0.1% $Ca(NO_3)_2$, 0.025% $KH_2PO_4$, 0.01% KCl, 0.03% $MgSO_4$, 0.001% $FeSO_4$, 0.0004% $ZnSO_4$; distilled water; pH 5.5; sterilization 30 min at 0.5 at. above atmospheric.

The flasks were then subjected to shaking under the same condition as before.

By means of the van Urk reaction 2470 mg alkaloids per liter were found to be in the culture medium after 14 days, calculated for ergotoxinebimaleinate. The alkaloids were then extracted with methylene chloride and were separated according to the method of Hohmann & Rochelmeyer (Arch. Pharmazie 297 (1965) p. 186/187) by thin layer chromatography through formamide impregnated kieselguhr. The UV spectrum was then determined photometrically. The medium was found to contain 1280 mg of ergotoxine 340 mg of ergometrine per liter. The remainder were two hitherto not defined native peptide alkaloids and simple ergoline derivatives such as Agroclavin, Chanoclavin, etc.

Parallel to this test there were determined the contents of alkaloids of the mycelium which had been separated by suction filtration and of the filtrate. It was found that the ergometrine was completely contained in the filtrate and that in addition 90% of the total ergotoxines was in the filtrate.

Example 5

Ten glass fermentors of 2 l contents were inoculated with a submerged spore culture made as in Example 2. The fermentors contained each 1.3 l nutrient solution A containing 10% saccharose, 1.5% ammoniumcitrate, 0.05% 0.05% $KH_2PO_4$, 0.03% $MgSO_4$, 0.001% $FeSO_4$ and 0.0004% $ZnSO_4$ in tap water (pH 5.5; sterilization 30 min. at 0.5 at above atmospheric).

The fermentation was effected at 24° C while stirring at 400 rpm with aeration of 0.3 l air/min. The contents of one of the fermentors was transferred after seven days into an 18 liter special steel fermentor containing 10 liters of a nutrient solution B. The latter solution contained 10% saccharose, 1.4% citric acid, 1.0% ammoniumhydroxide (25%), 0.05% $Ca(NO_3)_2$, 0.025% $KH_2PO_4$, 0.01% KCl, 0.03% $MgSO_4$, 0.001% $FeSO_4$ and 0.0004% $ZnSO_4$ in tap water; pH 5.5.

After an incubation at 24° C, 360 rpm and 2.5 l air/min. half of the contents of the fermentor was employed on the fifth day as inoculum for a 63 l special steel fermentor containing 40 l of a nutrient solution C. The solution C contained 20% saccharose, 1.75% citric acid, 0.075% $KH_2PO_4$, 0.02% KCl, 0.03% $MgSO_4$, 0.003% $FeSO_4$, 0.0012% $ZnSO_4$ in tap water; addition of ammoniumhydroxide at pH 5.3; sterilization 60 min. at 110° C.

The culture was subjected to stirring for 7 days at 24° C and 300 rpm and was aerated with 27 l of air/min. If necessary an antifoaming agent was added. At the end of the incubation the culture liquid contained 2640 mg of total alkaloids per liter.

An analysis carried out as in Example 4 showed that the contents comprised 1300 mg ergotoxine and 550 mg ergometrine.

Example 6

The inoculum in this case was a mass of spores grown as described in Example 3 and stored for 8 months at 4° C. The inoculum was placed in even portions in two special steel fermentors of 18 l contents. In each fermentor 10 l of nutrient solution A as defined in Example 5 was placed. The fermentors were subjected to aeration for 7 days at 24° C and were stirred at 360° rpm. The aeration was effected with 2.5 liters of air/min. The contents of the two fermentors was then transferred into a single 250 liter special steel fermentor which contained 180 liter of the nutrient solution B of Example 5. The mass was then subjected to incubation at 24° C and was stirred at 160 rpm and aerated with 0.5 liter air/liter nutrient solution × min. After 5 days the culture was transferred to a 2000 liter stainless steel fermentor filled with 1400 liter nutrient solution C as described in Example 5. The nutrient solution however additionally contained 0.0005% $NiSO_4$. The incubation was effected at 24° C, 160 rpm and 0.6 liter air/liter nutrient solution × min. If necessary in all fermentors an antifoaming agent was added.

The analysis showed that on the seventh day the culture contained 2430 mg of total alkaloids per liter of culture liquid. The further analysis carried out according to Example 4 showed a contents of 1150 mg ergotoxine and 490 mg ergometrine per liter of culture liquid.

Example 7

This example illustrates the obtaining of the desired products from a filtrate of the culture liquid. 200 liter of culture filtrate obtained from the culture liquid formed according to Example 6 which had been diluted by addition of water at a volume ratio of 1:1 prior to separation of the mycelium, were alkalized with 25% ammonia water to a pH of 8.5. The ergotoxin alkaloids and the ergometrine were then extracted with 50 liter of ethylacetate on a two-stage countercurrent extraction device. The ethylacetate extract was then concentrated in vacuum at a temperature below 30° C to 1/20 of the initial volume. The remaining mass was reacted with 2 parts by volume of chloroform and was permitted to stand for 15 hours at 4° C to cause crystallization of the ergometrine-chloroform adduct. This product was then removed by suction and there were obtained 35.4 g of a yellowish ergometrine-chloroform adduct at a yield of 75%.

This ergometrine-chloroform-adduct was then dissolved in the presence of activated carbon upon heating in 3.1 liter of acetone. To the filtrate the necessary amount of maleic acid solution in acetone was then added. The formed crystalline ergometrine bimaleinate was removed by suction and dried at 70° C. The alkaloid salt was obtained as a tlc-pure, white to yellowish, crystalline powder at a yield of 90% and with an alkaloid content of 98 to 100%. The specific rotation was $(\alpha)_D^{20} = +50°$ C (c = 1 in water). The ergotoxin-containing filtrate which remained after separating the ergometrine-chloroform adduct was then further concentrated to a volume of 0.297 liter. Thereafter the following different steps were taken in different runs of the experiment. They therefore represent alternative procedures.

(a) The filtrate was subjected to column chromatographied with ethyl acetate by using 20 times the amount of aluminum oxide of the activity stage 1 neutral relative to the total amount of alkaloids in the concentrate. Elution was then effected with 3.8 liter of the same solvent. After concentration by evaporation of the eluate in a vacuum at +30° C to dryness the residue in the amount of 74.2 g was converted to an ergotoxine-benzene adduct by taking it up in 0.212 liter of benzene and permitting the solution to stand for 15 hours at 4° C. The product that crystallized out was then removed by suction, washed with benzene and dried in a vacuum desiccator. There were obtained 55.2 g of tlc-pure, white crystalline ergotoxine-benzene adduct having an alkaloid content of 95%. The specific rotation was $(\alpha)_D^{20} = -183°$ (c = 1.8 in $CHCl_3$).

(b) The filtrate was stirred with 20 times the amount of aluminum oxide of the activity stage 1 neutral relative to the total amount of alkaloids in the concentrate until the mixture had a homogeneous color. After standing for 15 minutes the mixture was extracted 3 times with 3.82 liter each of ethyl acetate. The extracts were united and concentrated by evaporation at 30° C up to dryness. The further processing was the same as in (a) above. There were obtained 52.5 g of tlc-pure white crystalline ergotoxine-benzene adduct with an alkaloid content of 95%. The specific rotation was $(\alpha)_D^{20} = -183°$ (c = 1.8 in $CHCl_3$).

(c) The filtrate was subjected to column chromatography with ethyl acetate by using an amount of five times aluminum oxide of activity stage 1: neutral relative to the total amount of alkaloids in the concentrate and adding furthermore activated carbon (adsorption mean ratio aluminum oxide : activated carbon 5:1). Elution was effected with 4 liters of the same solvent. The further processing was the same manner as in (a) above. There were obtained 55 g of tlc-pure white crystalline ergotoxine-benzene adduct having an alkaloid content of 96%. The specific rotation was $(\alpha)_D^{20} = -183°$ (C = 1.8 in $CHCl_3$).

(d) The filtrate was stirred in a filtration stirrer with 3 liters ethyl acetate upon use of five times the amount of aluminum oxide of the activity stage 1 neutral (relative to the total amount of alkaloids) and upon addition of activated carbon (adsorption mean ratio between aluminum oxide and activated carbon 5:1). Thereafter extraction was effected twice with 2.5 liter each ethyl acetate and the combined extracts were concentrated by evaporation to dryness at 30° C. The further processing was the same as in (a) above. There were obtained 55 g of tlc-pure white crystalline ergotoxine-benzene adduct having an alkaloid content of 96%. The specific rotation was $(\alpha)_D^{20} = -183°$ (C = 1.8 in $CHCl_3$).

55.2 g of ergotoxine-benzene adduct obtained as in any of the aforementioned alternative procedures were dissolved upon slight heating in 830 ml of absolute ethanol whereupon the necessary amount of 0.5 molar ethanolic (absolute) ethanesulfonic acid was added, and after that 4.2 liters anhydrous ether were introduced. There formed a crystalizate which was removed by suction and dried at 70° C. There was obtained tlc-pure white crystalline ergotoxine-ethanesulfonate with a degree of purity of 98 to 100% at a yield of 95%.

Example 8

This example illustrates the extraction from the mycelium. 12.0 kg of a mycelium obtained by filtration of a corresponding amount of culture liquid were extracted within 3 hours at 20° C with 18 liters acetone. The aqueous-acetone extract separated by filtration was then adjusted by means of phosphoric acid to a pH of 2 to 3 and was degreased and purified by two extractions with 17 liters of petroleum ether and 11 liters of petroleum ether-xylene (volume ratio 1:1). The obtained heavy phase containing the alkaloids was extracted at a pH 8 to 9 (adjusted by ammonia water) with a total of 7 liters of ethylacetate. The top phase was washed with water at a ratio of 1:1 and was evaporated at 30° C to a volume of 0.70 liter. It was then reacted with 1.40 liter chloroform. After standing overnight at 4° C the precipitated slurry type residue was separated.

The filtrate was concentrated under the aforementioned conditions to 0.180 liter and was then subjected to chromatography through 1.100 kg aluminum oxide (activity stage I) with 2 liters ethylacetate. The eluate was concentrated by evaporation to dryness in vacuum and the dry residues were dissolved in 100 ml toluene, benzene or xylene. After standing overnight at 4° C the precipitated material was separated and dried in a vacuum desiccator. There were obtained 14.0 of white crystalline ergotoxine-toluene adduct with a degree of purity of 98 to 100%.

Example 9

10.0 Liters of the culture liquid produced in accordance with Example 5 were extracted with 25.0 liter of ethylacetate upon stirring and after addition of 10% by weight of ammonium sulfate. The extraction was effected at a pH of 8 to 9 at 20° C. The heavy biophase was discarded. The organic phase was extracted twice with 5.0 liters each of 2% phosphoric acid. The collected aqueous phases were then extracted after adjustment of the pH to 8 to 9 with ammonia water in two extractions with 5.0 liters each of ethylacetate. The organic phases were then concentrated by evaporation to 200 ml at +30° C. The residue was reacted with 400 ml chloroform. After standing overnight at 4° C the material which crystallized out was removed by suction and dried in a vacuum desiccator. There were obtained 4.20 grams (71.2% of the theoretical) of ergometrine chloroform adduct at a degree of purity of 90.7%.

The filtrate which was concentrated under conditions as given before to 120 ml was then subjected to chromatography with ethylacetate through 300 g of aluminum oxide (activity stage I). The eluate was concentrated by evacuation in vacuum to dryness. The residue was dissolved in 30 ml benzene and was permitted to stand overnight at a temperature below 10° C. The material that precipitated was removed by suction and dried in a vacuum desiccator. There were obtained 7.95 g (equal to 73.6% of the theoretical) white crystalline ergotoxine-benzene adduct having a degree of purity of 91.6%.

Example 10

The ergotoxine-benzene adduct formed in accordance with Example 7 in an amount of 50.0 g was hydrogenated in 0.7 liter of dioxane at 60° C at a hydrogen pressure of 50 atmospheres above atmospheric in a shaking or stirring autoclave provided with heating means in the presence of Raney nickel within a time of 2 hours. The solution of the formed 9,10-dihydroergotoxine was filtered off the catalyst and concentrated by evaporation to dryness in a vacuum. The hydrogenated base was then caused to crystallize out in ethylacetate at 4° C. The crystallizate was removed by suction and dried at 60° C. There were obtained 47.5 g (equal to 90% of the theoretical) tlc-pure white crystalline product in the form of the ergotoxine base with a degree of purity of 90%. The specific rotation was $(\alpha)_D^{20} = -45.6°$ (c = 2 in pyridine).

The crystalline dihydroergotoxine base was then put in 200 ml methanol and the necessary amount of 1-molar methanolic ethanesulfonic acid was added upon stirring. After a short time the alkaloid salt separated out in the form of crystals.

After separation by suction and drying of the product there were obtained 48.5 g (equal to 95% of the theoretical) of tlc-pure white crystalline dihydroergotoxine-ethanesulfonate having a degree of purity of 98 to 100%.

Example 11

7.20 g of the ergotoxine-benzene adduct obtained in Example 9 were hydrogenated in 250 ml 90% aqueous dioxane at 20° to 25° C upon exclusion of light using 2.9 g palladium-carbon (5%) as catalyst and employing a special circulatory device consisting of a hydrogenating vessel with supply and circulating ducts, a thermometer, an ejector, a gas supply tank and a laboratory tubing pump. The operation was carried out with a number of revolutions of 138.5 h$^{-1}$, an ejector partial vacuum of 120 mm H$_2$SO$_4$ column and an ejector nozzle diameter of 2 mm. The operation was effected in a time of 4 hours. The solution of the formed 9,10-dihydroergotoxine was filtered off the catalyst. The clear filtrate was concentrated in a vacuum rotation evaporator to dryness at a temperature below 30° C. The dry residue was dissolved in 35 ml chloroform an then mixed with 35 ml diethylether and was precipitated upon intensive stirring with 70 ml of saturated ether solution of maleic acid. There precipitated a dihydroergotoxine bimaleinate. The product was removed by suction, washed with 30 ml diethylether and dried immediately in a vacuum desiccator over phosphorus pentoxide. There were obtained 6.55 g (93.5% of the theoretical) of tlc-pure white crystalline dihydroergotoxine bimaleate with a degree of purity of 97.9%.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method for obtaining ergoline derivatives by a fermentation process, the said derivatives including alkaloids and 9,10-dihydrogenated alkaloids of the ergotoxine group and including ergometrine, and
the said process comprising
growing conidiospores under saprophytic conditions from a strain of *Claviceps purpurea* (Fr.) Tul. deposited under number IMET PA 130 at the Institute for Microbiology and Experimental Therapy at Jena, German Democratic Republic, then employing these spores as inoculum in a submerged culture in a culture medium under aerobic conditions, and at the completion of the cultivation extracting the formed alkaloids from the filtrate or from the mycelium or directly from the culture medium, and if 9,10-dihydrogenated alkaloids are wanted then subjecting the recovered alkaloids to a 9,10-dihydrogenation.

2. The method of claim 1 including the step of converting the recovered alkaloids to a pharmaceutically acceptable acid addition salt.

3. The method of claim 1 wherein the said extraction is effected, at a pH of 8 to 9 with a lower alkyl carboxylic acid ester.

4. The method of claim 3 wherein the adjustment of the pH is effected with ammonia or ammonium sulfate.

5. The method of claim 1 wherein the extraction is effected with a dilute aqueous acid.

6. The method of claim 1 wherein the culture medium is subjected to extraction at a pH of 8 to 9 with a lower alkyl carboxylic acid ester.

7. The method of claim 1 wherein the extraction is effected, after separating the mycelium by filtration of the culture medium, by reacting the filtrate with a chlorinated hydrocarbon or a lower alkyl carboxylic acid ester.

8. The method of claim 7 wherein the culture medium, prior to separation of the mycelium, is diluted with water at a 1:1 ratio.

9. The method of claim 1 wherein the mycelium is separated from the culture medium by filtration and the filtrate is then subjected to extraction with acetone.

10. The method of claim 9 wherein the extract obtained is adjusted to a pH of 2 to 3 with an aqueous acid and is then subjected to purification and defattening by means of a hydrocarbon compound.

11. The method of claim 10 wherein the hydrocarbon compound is petroleum ether or a petroleum etherxylene mixture.

12. The method of claim 9 wherein the aqueous filtrate is extracted at a pH of 8 to 9 with a lower alkyl carboxylic acid ester whereupon the extract is subjected to a water-wash.

13. The method of claim 1 wherein the obtained alkaloid extract is reconcentrated in vacuo at a temperature up to 30° C.

14. The method of claim 13 wherein chloroform in an amount of 1 to 3 parts by volume is added to the alkaloid concentrate whereupon the concentrate is subjected to cold storage at a temperature up to +10° C whereupon a crystallized ergometrine-chloroform adduct is quantitatively obtained by filtration.

15. The method of claim 14 wherein the formed ergometrine-chloroform adduct is converted to a pharmaceutically acceptable acid addition salt thereof.

16. The method of claim 14 wherein after separation of the ergometrine-chloroform adduct the alkaloid filtrate is reconcentrated in vacuo at a temperature up to 30° C.

17. The process of claim 13 wherein the alkali concentrate is subjected to purification by column chromatography or in a batch process with aluminum oxide and activated charcoal at a ratio of 5:1 of aluminum oxide to activated charcoal, the ratio of aluminum oxide to total alkaloids being between 1:5 and 1:20.

18. The method of claim 17 wherein the desorption in the chromatography is effected by means of a lower alkyl carboxylic acid ester, a chlorinated hydrocarbon, a two-component mixture of the aforesaid compounds or of said mixture together with an aromatic hydrocarbon.

19. The method of claim 18 wherein the eluate or extract of the chromatography is concentrated by evaporation to dryness in a vacuum at a temperature up to 30° C and a purified epimer-free adduct of ergotoxine-aromatics is caused to crystallize by adding an aromatic hydrocarbon thereto.

20. The method of claim 19 wherein the formed adduct of ergotoxine-aromatics is converted to a therapeutically acceptable acid addition salt.

21. The process of claim 20 wherein the ergotoxine-aromatics adduct is subjected to hydrogenation in the presence of Raney-nickel at a temperature of 50° to 70° C and a hydrogen pressure of 30 to 70 atmospheres above atmospheric in dioxane so as to obtain a pigment-free 9,10-dihydroergotoxine base which step is followed by conversion of the base to a therapeutically acceptable acid addition salt.

22. The method of claim 19 wherein the ergotoxine-aromatics adduct is subjected to hydrogenation in aqueous dioxane at atmospheric pressure and at a temperature of 20° to 30° C in the presence of a 5 to 10% palladium-charcoal catalyst so as to obtain a pigment-free 9,10-dihydroergotoxine base followed by conversion of the base to therapeutically acceptable acid addition salts.

* * * * *